US009925315B2

(12) United States Patent
Eubanks et al.

(10) Patent No.: US 9,925,315 B2
(45) Date of Patent: *Mar. 27, 2018

(54) ADAPTIVE TUBING CASSETTES FOR USE IN CONNECTION WITH INTERVENTIONAL CATHETER ASSEMBLIES

(71) Applicant: BOSTON SCIENTIFIC LIMITED, Hamilton (BM)

(72) Inventors: Shannon Eubanks, Woodinville, WA (US); Keith Schubert, Redmond, WA (US); Peter Bristol, Shoreline, WA (US); Patrick Vilbrandt, Edmonds, WA (US)

(73) Assignee: BOSTON SCIENTIFIC LIMITED, Hamilton (BM)

( * ) Notice: Subject to any disclaimer, the term of this patent is extended or adjusted under 35 U.S.C. 154(b) by 154 days.

This patent is subject to a terminal disclaimer.

(21) Appl. No.: 14/793,720

(22) Filed: Jul. 7, 2015

(65) Prior Publication Data
US 2015/0314049 A1   Nov. 5, 2015

Related U.S. Application Data

(63) Continuation of application No. 13/184,434, filed on Jul. 15, 2011, now Pat. No. 9,072,540, which is a
(Continued)

(51) Int. Cl.
*A61M 1/00*        (2006.01)
*A61M 25/00*       (2006.01)
(Continued)

(52) U.S. Cl.
CPC ......... *A61M 1/008* (2013.01); *A61B 17/3207* (2013.01); *A61B 17/320758* (2013.01);
(Continued)

(58) Field of Classification Search
CPC ............. F04B 43/1253; F04B 43/0072; F04B 43/082; F04B 43/12; F04B 43/1261;
(Continued)

(56) References Cited

U.S. PATENT DOCUMENTS 3,864,786 A   2/1975 Salice
3,952,368 A   4/1976 Zernig et al.
(Continued)

FOREIGN PATENT DOCUMENTS

EP   0319272 A2   6/1989
EP   0731275 A1   9/1996
(Continued)

OTHER PUBLICATIONS

Scott Patrick Jamagin, et. al., "Office Action dated May 29, 2014" for U.S. Appl. No. 13/184,434.

*Primary Examiner* — Bradley Osinski
(74) *Attorney, Agent, or Firm* — Seager, Tufte & Wickhem, LLP

(57) ABSTRACT

Peristaltic pump assemblies in which the closing and opening of a pivoting or sliding door is coordinated with movement of the occlusion bed toward and away from the rotor assembly to engage and disengage tubing within the occlusion pathway are disclosed. Linkage mechanisms provided by the interaction of cam surfaces with rollers, as well as bar linkage mechanisms, are disclosed. The linkage mechanism, in addition to providing precise displacement of the occlusion bed, may also provide an over-center feature that enhances safety and pump operation when the door is in a closed position. Latching mechanisms and sensors may be incorporated. Control consoles incorporating such peristaltic pump assemblies are described. Adaptive components such as tubing cassettes routing aspiration and/or infusion tubing in a predetermined configuration to mate with occlusion pathways in aspiration and/or infusion pump assemblies (Continued)

provided in various types of medical devices and control consoles are also provided.

20 Claims, 15 Drawing Sheets

Related U.S. Application Data continuation-in-part of application No. 12/854,834, filed on Aug. 11, 2010, now Pat. No. 8,388,582.

(60) Provisional application No. 61/399,744, filed on Jul. 16, 2010, provisional application No. 61/233,434, filed on Aug. 12, 2009.

(51) Int. Cl.
| | |
|---|---|
| *A61B 17/3207* | (2006.01) |
| *F04B 43/00* | (2006.01) |
| *F04B 43/12* | (2006.01) |
| *A61B 17/00* | (2006.01) |
| *A61B 17/22* | (2006.01) |
| *A61M 1/10* | (2006.01) |

(52) U.S. Cl.
CPC ........ *A61M 1/0058* (2013.01); *A61M 1/0064* (2013.01); *A61M 1/0066* (2013.01); *A61M 1/0072* (2014.02); *A61M 25/0054* (2013.01); *F04B 43/0072* (2013.01); *F04B 43/1253* (2013.01); *A61B 2017/00199* (2013.01); *A61B 2017/00482* (2013.01); *A61B 2017/22079* (2013.01); *A61M 1/1006* (2014.02); *A61M 1/1039* (2014.02); *A61M 2202/0014* (2013.01); *A61M 2205/12* (2013.01); *A61M 2209/084* (2013.01)

(58) Field of Classification Search
CPC .............. F04B 43/1292; F04B 43/1223; F04B 43/1276; F04B 43/1238; F04B 43/1215
See application file for complete search history.

(56) References Cited

U.S. PATENT DOCUMENTS

| | | | |
|---|---|---|---|
| 4,025,376 A | 5/1977 | Schirmer | |
| 4,035,093 A | 7/1977 | Redshaw | |
| 4,075,735 A | 2/1978 | Röck et al. | |
| 4,085,481 A | 4/1978 | Lautenschlager | |
| 4,155,362 A | 5/1979 | Jess | |
| 4,187,057 A | 2/1980 | Xanthopoulos | |
| 4,256,442 A | 3/1981 | Lamadrid et al. | |
| 4,500,269 A | 2/1985 | Jess | |
| 4,558,996 A | 12/1985 | Becker | |
| 4,655,197 A | 4/1987 | Atkinson | |
| 4,798,580 A | 1/1989 | DeMeo et al. | |
| 4,813,855 A | 3/1989 | Leveen et al. | |
| 4,824,339 A | 4/1989 | Bainbridge et al. | |
| 4,861,242 A | 8/1989 | Finsterwald | |
| 4,925,376 A | 5/1990 | Kahler | |
| 4,925,444 A | 5/1990 | Orkin et al. | |
| 4,977,646 A | 12/1990 | McCraw | |
| 5,082,429 A | 1/1992 | Soderquist et al. | |
| 5,106,366 A | 4/1992 | Steppe | |
| 5,181,842 A | 1/1993 | Sunderland et al. | |
| 5,195,960 A | 3/1993 | Hossain et al. | |
| RE34,556 E | 3/1994 | Sjostrom et al. | |
| 5,380,173 A | 1/1995 | Hellstrom | |
| 5,381,510 A | 1/1995 | Ford et al. | |
| 5,433,588 A | 7/1995 | Monk et al. | |
| 5,460,490 A | 10/1995 | Carr et al. | |
| 5,468,129 A | 11/1995 | Sundén et al. | |
| 5,484,239 A | 1/1996 | Chapman et al. | |
| 5,549,458 A | 8/1996 | Chapman et al. | |
| 5,588,815 A | 12/1996 | Zaleski, II | |
| 5,769,811 A * | 6/1998 | Stacey ................ | A61M 1/3693 604/4.01 |
| 5,845,530 A | 12/1998 | Brockmeyer et al. | |
| 5,927,956 A | 7/1999 | Lim et al. | |
| 5,928,177 A | 7/1999 | Brugger et al. | |
| 6,019,582 A | 2/2000 | Green | |
| 6,059,544 A | 5/2000 | Jung et al. | |
| 6,077,246 A | 6/2000 | Kullas et al. | |
| 6,494,693 B1 | 12/2002 | Sundén | |
| 6,511,454 B1 | 1/2003 | Nakao et al. | |
| 6,719,717 B1 | 4/2004 | Johnson et al. | |
| 6,722,865 B2 | 4/2004 | Domroese | |
| 6,926,726 B2 | 8/2005 | Drasler et al. | |
| 6,962,488 B2 | 11/2005 | Davis et al. | |
| 7,169,352 B1 | 1/2007 | Felt et al. | |
| 7,214,038 B2 | 5/2007 | Saxer et al. | |
| 7,238,010 B2 | 7/2007 | Hershberger et al. | |
| 7,239,916 B2 | 7/2007 | Thompson et al. | |
| 7,273,359 B2 | 9/2007 | Blight et al. | |
| 7,478,999 B2 | 1/2009 | Limoges | |
| D600,792 S | 9/2009 | Eubanks et al. | |
| 8,393,879 B2 * | 3/2013 | Kent .................. | F04B 43/1292 417/477.12 |
| 2005/0053502 A1 | 3/2005 | Souza | |
| 2007/0073233 A1 | 3/2007 | Thor et al. | |
| 2007/0243088 A1 | 10/2007 | North | |
| 2007/0253850 A1 | 11/2007 | Williams | |
| 2008/0154095 A1* | 6/2008 | Stubkjaer ............ | A61M 3/0258 600/156 |
| 2008/0175734 A1 | 7/2008 | LaBanco et al. | |
| 2009/0129944 A1 | 5/2009 | Stemple et al. | |
| 2009/0192498 A1* | 7/2009 | Andrew ............ | A61B 17/3203 604/542 |
| 2013/0131585 A1 | 5/2013 | Eubanks et al. | |

FOREIGN PATENT DOCUMENTS

| | | |
|---|---|---|
| EP | 1947340 A1 | 7/2008 |
| EP | 001156335-0001 | 7/2009 |
| JP | 1385142 | 3/2010 |
| WO | 2008042987 A2 | 4/2008 |

* cited by examiner

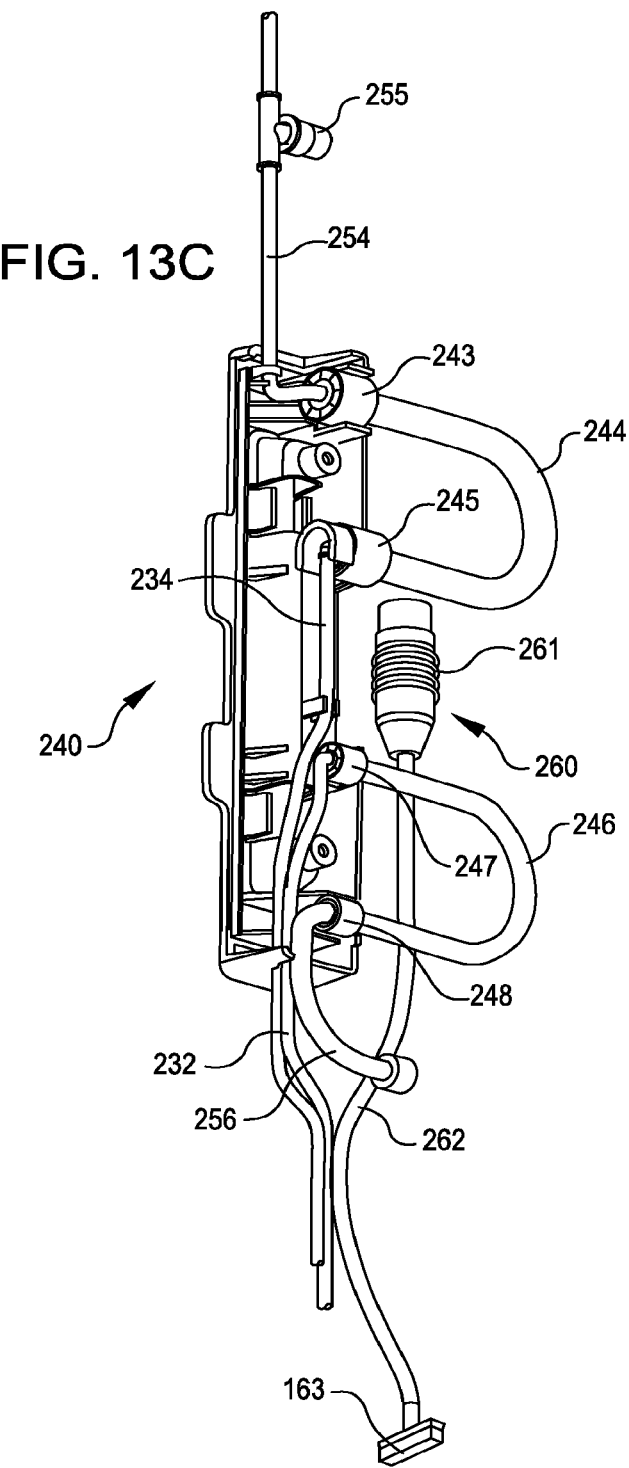

ADAPTIVE TUBING CASSETTES FOR USE IN CONNECTION WITH INTERVENTIONAL CATHETER ASSEMBLIES

REFERENCE TO PRIORITY APPLICATIONS

This application is a continuation of U.S. patent application Ser. No. 13/184,434 filed Jul. 15, 2011, now U.S. Pat. No. 9,072,540, which claims priority to U.S. Provisional Patent Application No. 61/399,744 filed Jul. 16, 2010, and is a continuation-in-part of U.S. patent application Ser. No. 12/854,834 filed Aug. 11, 2010, now U.S. Pat. No. 8,388,582, which claims priority to U.S. Provisional Patent Application No. 61/233,434 filed Aug. 12, 2009. The disclosures of these priority applications are incorporated by reference herein in their entireties.

FIELD OF THE INVENTION

The present invention relates generally to peristaltic pump housing and component configurations, and peristaltic pump assemblies, in which the closing and opening of a pivoting or sliding door is coordinated with movement of the occlusion bed to engage and disengage tubing within the occlusion pathway. The present invention also relates to systems incorporating peristaltic pump assemblies and adaptive tubing cassettes that interface with the peristaltic pump assemblies for use in a wide range of medical device applications.

BACKGROUND OF THE INVENTION

Peristaltic pumps are well known and used in many research, medical and industrial systems and applications for pumping fluids, slurries and other materials. Rotary peristaltic pumps are positive displacement pumps that generally move fluids through flexible tubing positioned in a pathway formed between pump rollers and an occlusion bed by the action of rollers contacting the external surface of the tubing to compress the tubing against the occlusion bed, thereby moving fluids, slurries and other materials through the tubing. The occlusion bed may be moved between an open condition in which tubing may be inserted into the pathway prior to and removed from the pathway following pump operation, and a closed condition in which the tubing is retained between the rollers and the occlusion bed during pumping operations. Many schemes and arrangements have been implemented to facilitate mounting of tubing in the pathway and removal of tubing from the pathway.

U.S. Patent Publication 2009/129944 discloses a peristaltic pump having an occlusion bed slideably mounted in the pump housing. When a pivoting door is opened, the occlusion bed slides away from the rotor assembly to permit mounting of tubing and when the pivoting door is closed, the occlusion bed slides toward the rotor assembly to clamp the tubing in position for pump operation. A rack and pinion arrangement coordinating movement of the sliding occlusion bed with pivoting of the door is disclosed. A sensor may be configured to sense the door condition and disable the peristaltic pump when the door is in an open condition. Additional tube retainer systems for use with peristaltic pumps are described, for example, in U.S. Pat. Nos. 4,558, 996, 4,025,376, and 6,722,865, European Patent Application EP 0 731 275 and U.S. Patent Publications 2008/175734 and 2007/243088.

Many material removal devices and interventional catheters incorporate mechanical aspiration systems to remove fluid, disease material and/or particulate debris from the site. Some systems incorporate, or are used in conjunction with, other mechanisms such as distal filters, for preventing material dislodged during the procedure or debris generated during the procedure from circulating in the blood stream. Some interventional catheter systems incorporate or are used in conjunction with a fluid infusion system providing delivery of fluids to an interventional site. Interventional catheter systems may also incorporate or be used in conjunction with imaging systems and other types of complementary and/or auxiliary tools and features that facilitate desirable placement and operation of the system during an interventional procedure.

Some interventional catheter systems employ a console-type controller that interfaces directly with interventional catheter components, while some interventional catheter systems employ both a console-type controller that houses non-disposable components such as pumps, drive systems, electrical, electronic, vacuum and fluid control systems, and the like, as well as another intermediate control device that provides operator control options and, in some cases, feedback information. The intermediate control device is typically located at or near a proximal end of the interventional catheter, and may be positioned within or close to the sterile field during a procedure. Interventional catheter systems employing both a console-type controller and an intermediate control device are described, for example, in PCT International Publication WO 2008/042987 A2, the disclosure of which is incorporated herein by reference in its entirety.

During setup of an interventional catheter system employing a control module, an operator typically connects or otherwise operably interfaces components of the interventional catheter assembly, or an intermediate control system generally designed for single patient use, to the reusable console-type control module. In many cases, this involves installing infusion and/or aspiration tubing in the console, interfacing the tubing with pump(s), infusion sources and aspiration receptacles, priming the infusion system, and the like. Providing simple to operate interfaces between infusion and/or aspiration tubing, pumps, sources and receptacles, while also providing accurate and reliable placement of tubing and maintaining appropriate tolerances is essential to pump operation and, ultimately, the success and outcome of interventional operations. Pump assemblies and systems incorporating these pump assemblies of the present invention are directed to achieving these objectives.

SUMMARY OF THE INVENTION

Peristaltic pump components, component configurations and pump assemblies for use in a wide range of applications, including medical device applications, are disclosed. In general, pump and pump housing component configurations in which the closing and opening of a pivoting or sliding door is coordinated with movement of the occlusion bed to engage and disengage tubing within the occlusion pathway are provided. The component configurations and coordinated movement of a pivoting or sliding door with a slidable occlusion bed provide clearance to conveniently insert and remove tubing from the occlusion pathway, while providing positive and reliable and precise positioning and retention of tubing in the occlusion pathway during operation of pump. The pump components, component configurations and assemblies may be used with a variety of tubing types and pump capacities, providing a wide range of pump pressures, volumes, flow rates, and the like.

Pump assemblies and components of the present invention incorporate a linkage mechanism that coordinates sliding of the occlusion bed toward and away from the pump rotor assembly in concert with movement of a door toward and away from the rotor assembly. In one embodiment, the linkage mechanism coordinates sliding of the occlusion bed in concert with pivoting of a door and is provided by the interaction of cam surfaces with rollers. In this embodiment, cam surfaces may be mounted in a fixed condition on the pivoting door, or on a component mounted on the pivoting door, and rollers configured and positioned to interact with the cam surfaces may be mounted, directly or indirectly, to the occlusion bed. As the door is pivoted from an open condition toward the rotor assembly, curved portions of the cam surfaces contact the rollers to displace the rollers, and the occlusion bed, toward the rotor assembly. A spring mechanism is generally provided to bias the sliding occlusion bed away from the rotor assembly and, as the door is pivoted from a closed condition toward an open condition, curved portions of the cam surfaces contact the rollers and allow the spring mechanism to draw the sliding occlusion bed away from the rotor assembly. The profile and positioning of the cam surfaces may be designed to provide a desired extent of displacement of the sliding occlusion bed, with a desired force, and may also provide an over-center feature that reduces the load and enhances safety and pump operation as the pivoting door approaches the closed position and when the pivoting door is in the closed position.

In another embodiment in which the linkage mechanism coordinates sliding of the occlusion bed in concert with pivoting of a door, the linkage mechanism is provided as a bar linkage system in which at least two bars are pivotably mounted, directly or indirectly and at opposite ends, to the pivoting door and to the sliding occlusion bed. In this embodiment, one end of each of a set of bars may be mounted for pivoting on a first pivot axis on the pivoting door, or on a component mounted on the pivoting door, and the other end of each of a set of bars may be mounted, directly or indirectly, to the occlusion bed for pivoting on a second pivot axis. As the door is pivoted from an open condition toward the rotor assembly and to a closed position, the linkage bars are displaced, thereby displacing the occlusion bed, toward the rotor assembly. As the door is pivoted from a closed condition toward an open condition and away from the rotor assembly, the linkage bars are displaced away from the rotor assembly, thereby displacing the occlusion bed away from the rotor assembly. The dimensions and placement of the linkage bars may be designed to provide a desired extent of displacement of the sliding occlusion bed, and the pivot axes of the linkage bars and pivoting door may be arranged to provide an over-center feature that reduces the load and enhances safety and pump operation when the pivoting door approaches the closed position and is in the closed position.

In alternative embodiments, pump assemblies comprise a linkage mechanism that coordinates the sliding of the occlusion bed with a door that slides in one direction to provide access to the occlusion pathway and in another direction to prohibit access to the occlusion pathway. The linkage mechanism may, for example, comprise a pair of linkage beams pivotably mounted at one end to a stationary frame member and at another end to a sliding door or cover. The sliding occlusion bed is linked to at least one of the beams so that it follows a lateral component of the path traveled by the bars as the door or cover slides. Thus, as the door or cover slides, the linkage bars pivot, both at their linkage to the sliding door or cover and at their linkage to a stationary frame member, and the sliding occlusion bed moves along a defined lateral path toward and away from the rotor assembly.

Suitable latching mechanisms may be provided to prevent inadvertent opening of the door and disruption of the tubing during pump operation. In one embodiment, one or more magnetic latches may be provided and positioned in mechanical components mounted, directly or indirectly, to the door and to the pump housing, or to a support structure associated with the pump housing, to provide alignment of the door with the pump housing as well as positive latching. Sensing devices may also be provided to sense when the door is fully closed. Such sensing devices may enable pump operation when the door is fully closed and disable pump operation when the door is fully or partially open.

One or more pump assemblies of the present invention may be used in connection with medical devices incorporating infusion and/or aspiration systems. In one embodiment, one or more pump assemblies is mounted in a control console that houses certain interventional catheter assembly operating systems, such as aspiration and/or infusion systems, and interfaces with a medical device, such as an interventional catheter, to provide suitable aspiration and/or infusion pressures to appropriate interventional catheter lumens, to provide power to the interventional catheter as necessary, and the like. A common control console incorporating one or more pump assemblies of the present invention may be used to operate an aspirating interventional catheter, such as a thrombectomy device, as well as simple infusion catheters and atherectomy and thrombectomy devices that operate using either or both aspiration and infusion systems. The control console may also incorporate other operating and control features, drive systems, power supplies, and the like, that may interface with an interventional catheter assembly.

In another aspect, adaptive components such as tubing cassettes having various configurations may be provided for operating different types of medical devices, such as interventional catheters, using a control console. In one embodiment, for example, a tubing cassette having a housing through which aspiration and/or infusion tubing is conveyed, is provided for interfacing with aspiration and/or infusion systems having pump assemblies provided on a control console. Adaptive tubing cassettes are designed to facilitate positioning of the aspiration and/or infusion tubing in the occlusion pathway. The tubing cassette may route aspiration and/or infusion tubing in a predetermined configuration to mate with the occlusion pathway(s) in aspiration and/or infusion systems on the control console, and may also mate with a mechanical interface provided on the control console to provide stable mounting of the tubing cassette during pump operation. The size, configuration, composition and positioning of tubing loop(s) may be selected based on the type of aspiration and/or infusion system used, the position and configuration of the occlusion pathway, desired pump configurations, operating infusion and/or aspiration volumes and pressures, and the like.

BRIEF DESCRIPTION OF THE DRAWINGS

FIG. 13C shows a perspective view of the exemplary interventional catheter tubing cassette of FIG. 13A with a portion of the housing removed to illustrate the interior of the tubing cassette.

Like numbers have been used to designate like parts throughout the drawings to provide a clear understanding of the relationship of the various components and features, even though different views are shown. It will be understood that the appended drawings are not necessarily to scale, and that they present a simplified, schematic view of many aspects of systems and components of the present invention. Specific design features, including dimensions, orientations, locations and configurations of various illustrated components may be modified, for example, for use in various intended applications and environments.

DETAILED DESCRIPTION

Figure 1:
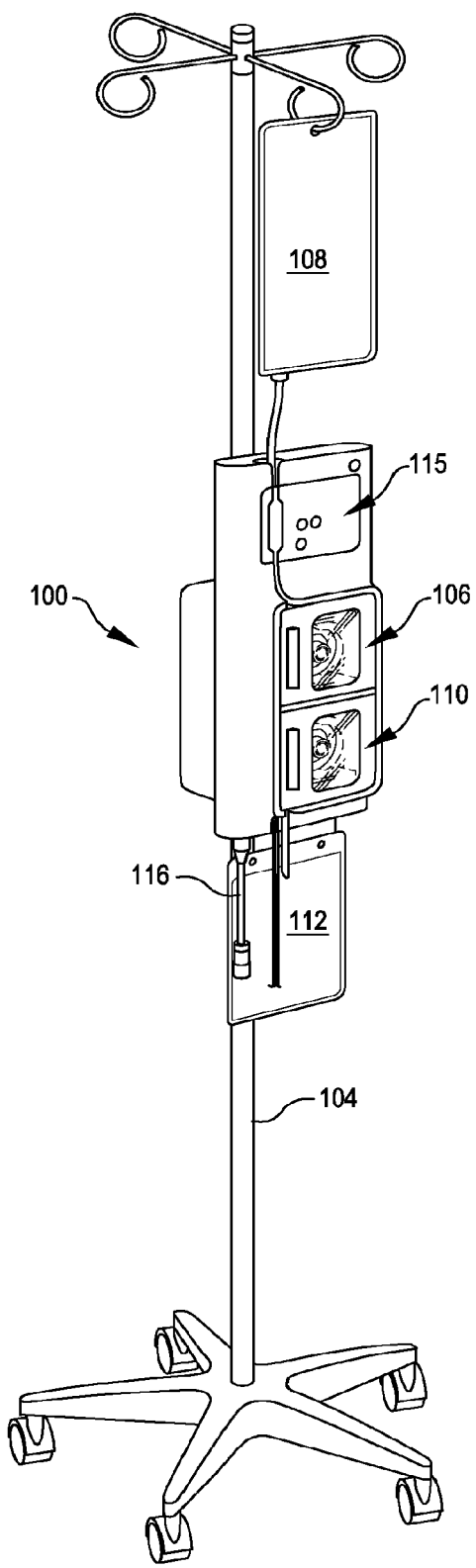
FIG. 1 shows a schematic view of an exemplary interventional catheter control console of the present invention comprising aspiration and infusion systems and showing an infusion source and an aspiration receptacle.

FIG. 1 illustrates an exemplary interventional control console 100 mounted, with an accessory infusate reservoir and aspirate receptacle, on a portable IV pole platform 104. In the embodiment illustrated in FIG. 1, control console 100 incorporates an infusion system 106 in fluid communication with an infusate source reservoir 108, such as a sealed fluid bag, and an aspiration system 110 in fluid communication with an aspirate collection receptacle 112. In the embodiment illustrated, and in preferred embodiments, at least one, and preferably both of the infusion and aspiration systems comprise peristaltic pumps arranged in a vertically stacked relationship. In one preferred embodiment, infusion system 106 comprises a high pressure peristaltic pump capable of infusing fluid at a rate of up to 150 ml/min at a pressure of up to about 160 psi. In another preferred embodiment, aspiration system 110 comprises a generally lower pressure peristaltic pump capable of aspirating liquid and/or liquid/solids mixtures at a rate of at least about 45 ml/min and up to about 90 ml/min at a pressure of up to about (−)15 psi.

Control console 100 may house other system operating systems and components as well, and typically houses complex or bulky operating and control systems that are impractical to provide in single use interventional catheter assemblies, or that cannot be readily sterilized. Control console 100 generally draws power from an external electrical system and generally incorporates a control panel 115 providing a user interface for interacting with operating and control systems housed in control console 100, and for monitoring system operating conditions. In one embodiment, control panel 115 provides a key pad interface for user selection of selectable options and LED indicators for displaying device operational status. Console subassembly 100 may house other system operating systems and components as well, and typically houses complex or bulky operating and control systems that are impractical to provide in single use interventional catheter assemblies, or that cannot be readily sterilized. Console subassembly 100 generally draws power from an external electrical system through electrical cable 116 or may house an independent electrical source.

Figure 2:
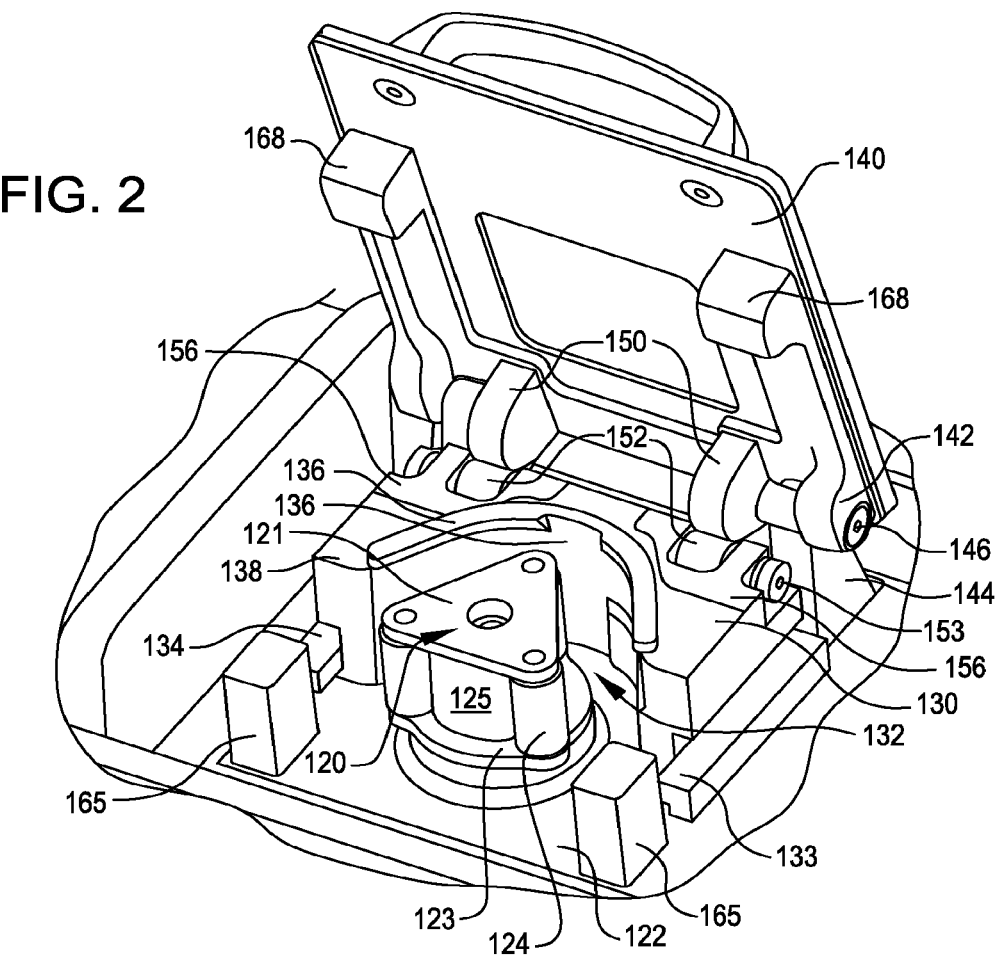
FIG. 2 shows a schematic perspective view of a rotor assembly, sliding occlusion bed, pivoting door and cam mechanism for moving the occlusion bed with respect to the rotor assembly as the pivoting door opens and closes.
Figure 6:
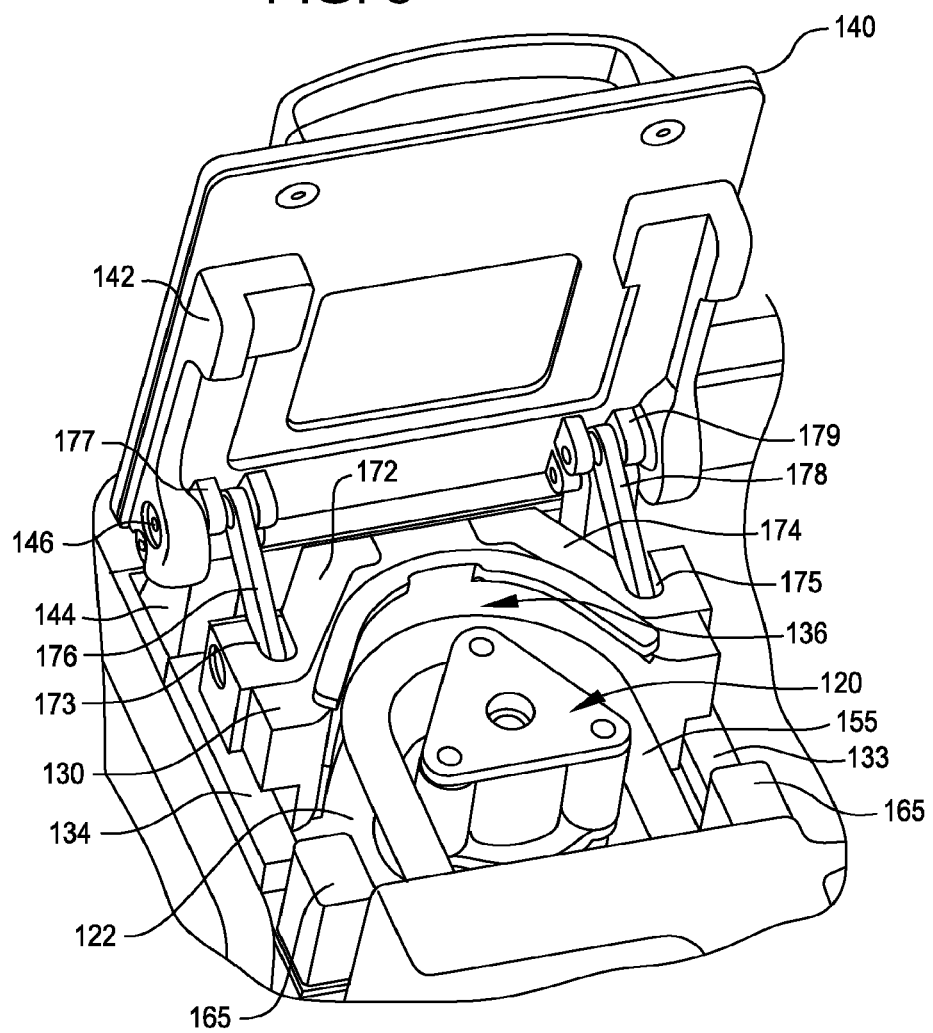
FIG. 6 shows a top perspective view of a rotor assembly with a tubing section positioned in the occlusion pathway, a sliding occlusion bed, pivoting door, and linkage mechanism for moving the occlusion bed with respect to the rotor assembly as the pivoting door is moved toward and away from the rotor assembly.
Figure 7:
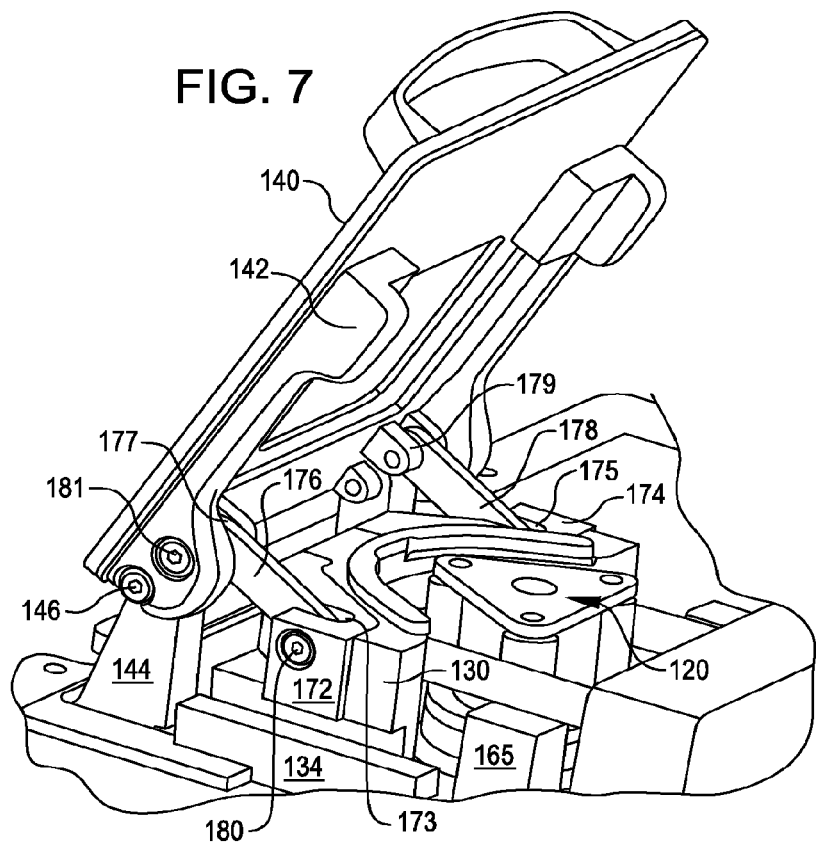
FIG. 7 shows a side perspective view of the assembly illustrated in FIG. 6.
Figure 8:
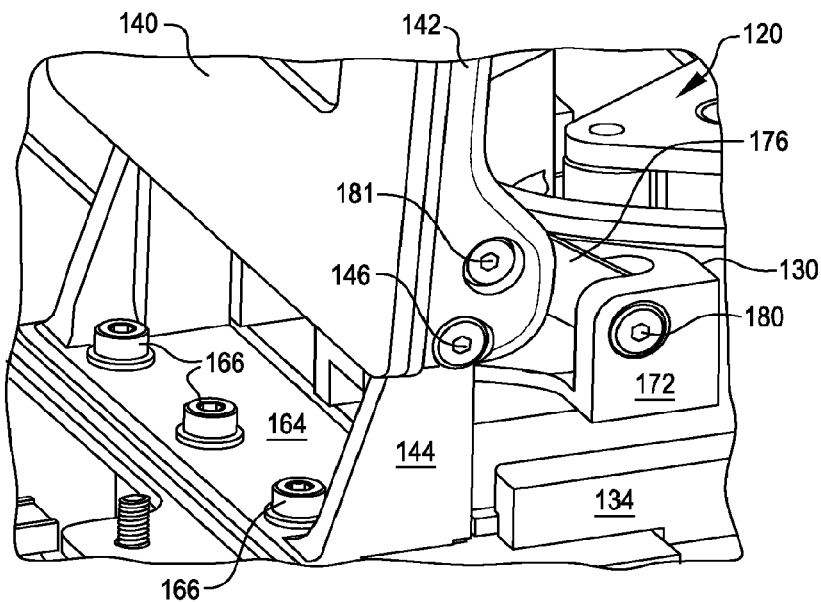
FIG. 8 shows a side perspective, enlarged view of a part of the linkage mechanism shown in FIGS. 6 and 7.

Infusion system 106 and aspiration system 110 each incorporate at least one pump rotor assembly mounted on a face of the console subassembly, shown in greater detail in FIGS. 2, 6 and 7. The pump rotor assembly 120 comprises a rotor housing mounted on a peristaltic pump motor shaft (not shown) for rotation, as a unit, with respect to mounting plate 122. Pump motor is mounted underneath mounting plate and rotor assembly 120 is mounted on peristaltic pump motor shaft. The pump motor shaft, or a portion of it, is generally received in a central enclosure of the pump housing and suitable bearings, flanges, and the like are provided for rotation of pump rotor assembly 120 with respect to mounting plate 122. The rotor housing may comprise an upper plate 121 and a lower plate 123 between which a plurality of rollers 124 are independently and rotatably mounted on rotor shafts (not shown). The rotor housing is preferably conveniently disassembleable to allow cleaning and maintenance of the rollers, bearings, and the like.

In some embodiments, the position of the rotor housing and rotor assembly may be adjustable with respect to the position of the occlusion pathway and the occlusion bed to facilitate adjustment of the occlusion gap. In yet other embodiments, a sensor may be provided that directly or indirectly senses the relative rotational position of the rotor assembly. This sensor allows the rotor assembly to be preferentially stopped at one of a plurality of predetermined relative angular positions provides convenient loading of tubing between the pump rotor assembly and the occlusion bed.

Rotor assemblies incorporating three rollers are preferred for use in the present invention, although additional rollers (e.g., four, five, or more) may be used and spaced equidistantly from one another, with their outer surfaces circumscribing a circle. The rollers preferably have equal dimensions and preferably have a diameter from between about 8 and about 15 mm and, in some embodiments, rollers having a diameter of about 11.5 mm are provided. The rollers are preferably constructed from a rigid, hard, durable and chemically resistant material such as a stainless steel material. Rotor assemblies comprising three equidistantly spaced rollers are preferred for use in assemblies and devices of the present invention for ease of loading and operation, and to provide suitable pillow volumes. In general, the same or similar rotor assemblies may be used for both aspiration and infusion pumps.

FIGS. 2-5B show one embodiment of an occlusion mechanism for moving an occlusion bed toward and away from the rotor assembly as a door is pivoted toward the closed and open condition, respectively. In the embodiment shown in FIG. 2, rotor assembly 120 is mounted for rotation on support plate 122 and occlusion bed 130 is slidably mounted for movement toward and away from rotor assembly 120, e.g., by sliding on mounting plate 122 or another base plate between rails 133, 134. Rails 133, 134 are preferably aligned parallel to one another and mounted to provide tight clearance with sliding occlusion bed 130, allowing occlusion bed 130 to move along a path toward and away from the rotor assembly. The sliding occlusion bed preferably incorporates grooves that match the configuration and profile of rails 133, 134, or another complementary interface with a cooperating structure that provides consistent and precise sliding of occlusion bed 130 along a path toward and away from rotor assembly 120.

Occlusion bed 130 has curved tubing interface surface 136 that, during peristaltic pump operation and rotation of rotor assembly 120, serves as a stationary curved surface against which the rollers press the tubing to advance and pump fluids in the tubing. The occlusion bed interface surface profile is generally curved along a segment to form a curve substantially similar to, and spaced apart from, the curve formed by a circle circumscribing the outer surfaces of the rollers of the rotor assembly. Occlusion pathway 132 is formed between occlusion bed tubing interface surface 136 and outer surfaces of rotor assembly rollers. A projecting rim 138 is provided at an upper surface of the occlusion bed 130 in the embodiment illustrated in FIG. 2, which overhangs the occlusion pathway and the tubing interface surface and assists in keeping tubing centered in the occlusion pathway during rotation of the rotor assembly and operation of the pump. The occlusion bed geometry is preferably such that occlusion bed surfaces at the end of each pillow segment are tangent to the corresponding roller contact point, and the gap between the tubing and the occlusion bed is constant along the entire pillow segment. Occlusion gaps of between about 0.120 in. and 0.170 in. are suitable for many applications; occlusion gaps of between about 0.150" and about 0.160" are preferred for many embodiments.

Occlusion bed 130 is preferably constructed from a substantially rigid, durable, impact, fatigue and chemically resistant material that is at least somewhat lubricious, at least in the area of the occlusion pathway. Materials having a dynamic coefficient of friction of from about 0.10 to 0.40, and more preferably from about 0.15 to 0.25 are preferred materials for providing at least tubing interface surface 136 and have been found to reduce tubing wear and degradation during operation of the pump. Generally lubricious materials such as acetal resins, including various Delrin® materials, are preferred for use in some embodiments. In some embodiments, an occlusion bed assembly comprises a generally lubricious tubing interface surface stably mounted to a support structure composed of a material having greater stiffness properties, or lower deformation properties, than those of the tubing interface surface. This arrangement has been found to facilitate the high tubing compression forces required for high pressure pumping applications.

Figure 3:
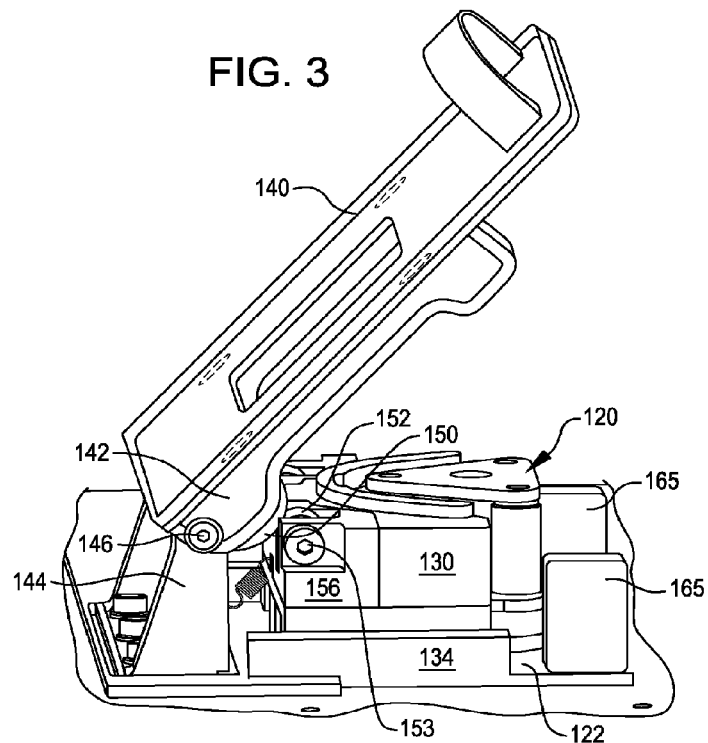
FIG. 3 shows a side perspective view of the rotor assembly, sliding occlusion bed, pivoting door and cam mechanism shown in FIG. 2.

Pivoting door 140 is mounted to hinge brackets 144 for pivoting the door toward and away from rotor assembly 120. Hinge bracket(s) 144 are generally mounted to mounting plate 122 or another structure that remains stationary during operation of the motor and during opening and closing of the door. In the embodiments illustrated in FIGS. 2-4, opposing hinge brackets 144 are provided and mount directly to door 140 or indirectly to a door frame 142 for rotation of the door around pivot axis 146. Hinge brackets 144 may be provided on an integral structure, as shown in FIGS. 2-4, or separate brackets may be provided opposite one another for mounting to opposite sides of door 140.

In the embodiment shown in FIGS. 2-5B, mating cams 150 are mounted on the underside of pivoting door 140 in the vicinity of hinge brackets 144. As door 140 pivots about pivot axis 146, cams 150 contact rollers 152 mounted in alignment for contact with the respective cam interface surfaces. In the illustrated embodiment, rollers 152 are mounted for rotation around axes 153 in roller mount supports 156. Roller mount supports 156 are mounted in mating cutouts provided opposite corners of occlusion bed 130 and, in the illustrated embodiment, provide continuous surfaces in combination with the occlusion bed. In an alternative embodiment, roller mount supports may be provided directly in a portion of the occlusion bed itself as integral components of the occlusion bed. Additional alternative structures and constructions may be contemplated and used, provided that the rollers and roller mount supports are mounted for movement (e.g., displacement or translation) with occlusion bed 130. Cams and rollers are generally high wear components, made from rigid, hard, highly impact, fatigue and chemically resistant materials such as stainless steels. The roller mount supports may provide a highly rigid support structure having greater stiffness properties than those of the tubing interface surface of occlusion bed 130, as described previously. This arrangement is particularly suitable for use in pump assemblies used in high pressure pumping applications.

Figure 4:
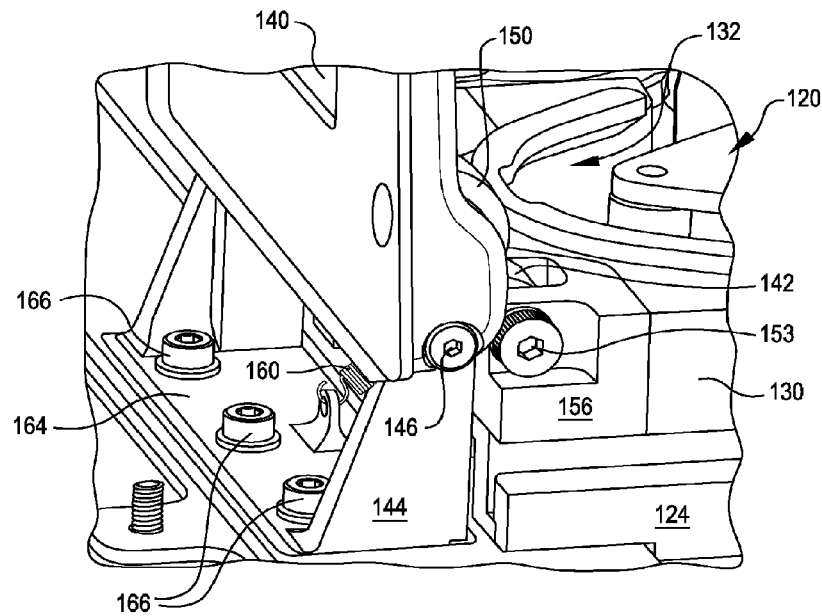
FIG. 4 shows a side perspective, enlarged view of a part of the pivoting door, cam and roller mechanism shown in FIG. 3.

FIG. 4 shows an enlarged view of hinge bracket 144, occlusion bed 130 slidably retained along rail 124, pivoting door pivot axis 146, roller mount support 156, roller 152 and cam 150 in the door open, occlusion pathway open condition. This embodiment also shows a spring 160 biasing occlusion bed 130 and stationary mounting bracket 144 toward hinge bracket(s) 144 so that, as the door 140 is pivoted toward a closed position and the occlusion bed 130 is displaced toward the rotor assembly by action of the cam surfaces on rollers 142, the cam and roller surfaces remain in positive contact and tension. During opening of the pivoting door 140 and when the pivoting door is in an open condition, the spring mechanism 160, which may be any type of spring or biasing mechanism, biases the occlusion bed 130 and components associated with the occlusion bed, toward the hinge bracket to maintain the appropriate separation between the occlusion bed tubing contact surface 136 and the rotor assembly 120, allowing removal of tubing from and insertion of tubing into the occlusion pathway 132. During closing of the pivoting door and when the pivoting door is in a closed position, the spring mechanism is extended and maintains tension on the occlusion bed as the occlusion bed is displaced toward the rotor assembly by the action of the cam surfaces on rollers 142.

FIG. 4 also illustrates a system for adjusting the dimension of the occlusion gap or passageway. Adjustment of the occlusion gap may be desirable to accommodate different sizes and types of tubing, and to modify the pressures exerted on the tubing during operation of the pump. In this embodiment, hinge bracket(s) 144 is mounted on or provided integrally with an adjustment plate 164 mounted directly, or indirectly, to support plate 122. Adjustment plate 164 thus remains stationary with respect to support plate 122 and roller assembly during pivoting of the door and displacement of the occlusion bed. Adjustment plate 164 may be mounted in a cavity, or slot, permitting displacement of the adjustment plate toward and away from the rotor assembly. One or more set screws 166 may be provided for mounting adjustment plate 164 in a desired location and setting the desired occlusion gap for a particular device, interventional procedure, tubing type, pump pressure or volume, or the like, thereby changing the location of the cam surfaces and, through the spring mechanism, additionally adjusting the location of the roller surfaces, roller mount supports and occlusion bed with respect to the rotor assembly.

Figure 5A:
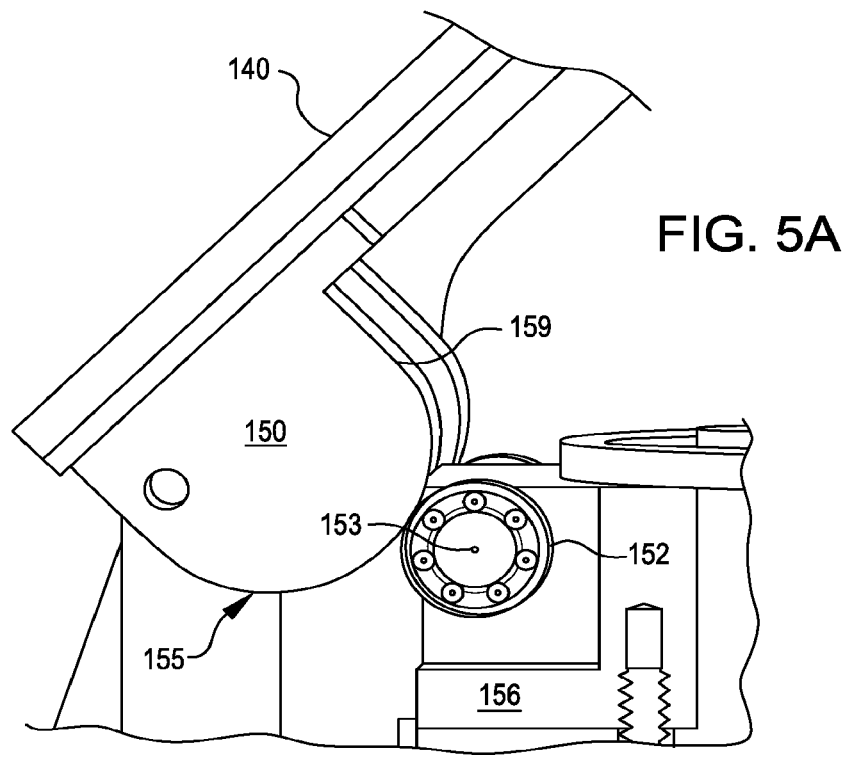
FIGS. 5A and 5B show enlarged side perspective views of the cam mechanism and mating roller(s) in the door open and door closed conditions.
Figure 5B:
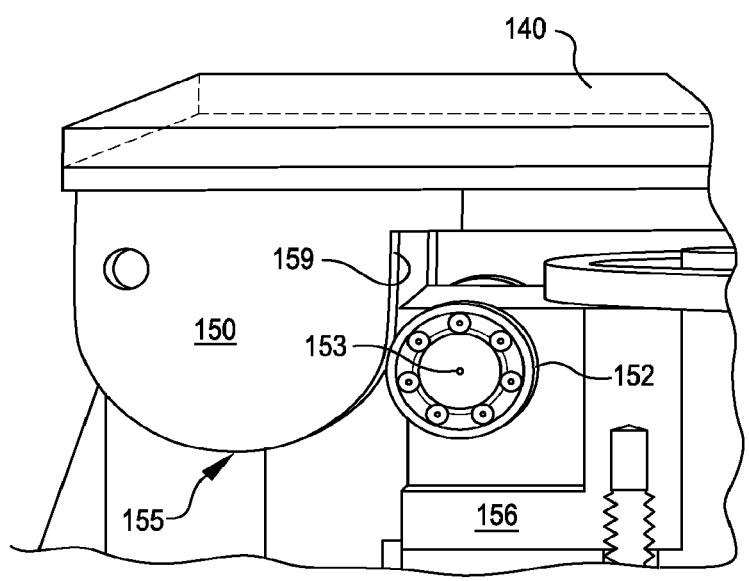

FIGS. 5A and 5B show an enlarged, partially cut-away view of the surfaces of cam 150 interfacing with the mating surfaces of roller 152 during closing of the door (FIG. 5A) and when the door is fully closed (FIG. 5B). The cam surfaces 155 that contact the roller surfaces during opening and closing of the pivoting door are generally curved, or may comprise a plurality of generally short linear sections that, in combination, approximate a curved surface. The profile of the cam surfaces may be chosen, and adjusted, to customize the force curve and the force generated by interaction of the cam surface with the roller. In one embodiment, the linkage mechanism provided by the interaction of the cam and roller surfaces provides a linear actuation relationship between the angle of the pivoting door and the position of the occlusion bed. This arrangement requires progressively greater force to pivot the door as it approaches the closed position and to move the occlusion bed as it contacts tubing in the occlusion pathway.

In another embodiment, the linkage mechanism provides a non-linear actuation relationship between the angle of the pivoting door and the position of the occlusion bed. Non-linear actuation relationships may be designed to provide an over-center feature that results in progressively greater mechanical advantage (i.e. progressively less force required for door pivoting and occlusion bed movement) as the door approaches the closed position and the occlusion bed approaches, and contacts, tubing in the occlusion pathway. Providing a flat cam surface 159 at the location where the roller contacts the cam when the door is in a closed position, as shown in FIG. 5B, provides an over-center design, which facilitates positive positioning of the door when closed and minimizes the chance of the door opening inadvertently during operation of the pump.

Latching mechanism(s) may also be provided to provide positive positioning of the door when closed and to reduce the chance of the door opening inadvertently during pump operation. Many different types of latching mechanisms may be used including, for example, magnetic latches. In the embodiments illustrated in FIGS. 2 and 3, magnets may be mounted in posts 165 positioned opposite the roller assembly 120 from occlusion bed 130, with additional magnets mounted in a door framework or posts 168. Posts 165 and 168 are positioned in proximity to one another when door 140 is in a closed position, with the magnets serving a latching function to maintain the door in the closed position until sufficient force is exerted to break the magnetic attraction. In the embodiment illustrated in FIG. 2, posts 165 are independent of one another; in alternative embodiments, the posts may be provided on a unitary structure mounted directly or indirectly to mounting plate 122 and having a structure intermediate the posts. The intermediate structure may provide support and/or guidance for tubing during operation of the rotor assembly and pump.

One or more sensors may also be provided in pump assemblies of the present invention for sensing when the pivoting door is in a closed and/or open condition. Suitable sensors are well known in the art. The sensor(s) may communicate with control mechanisms to provide safety and control features. In one embodiment, for example, movement of the rotor assembly is enabled only when the pivoting door is fully closed and the sensor confirms the closed condition. In another embodiment, movement of the rotor assembly is disabled in all door positions other than when the door is fully closed and the sensor(s) activated.

FIGS. 6-9B schematically illustrate another embodiment of components and a system for moving an occlusion bed toward and away from the rotor assembly as a door is pivoted toward and away from the rotor assembly to a closed and an open condition. Unless noted otherwise in the disclosure provided below, components that are similar to or common with those described above in connection with FIGS. 2-5B are labeled similarly and are not described in detail below.

In the embodiment shown in FIGS. 6 and 7, rotor assembly 120 is mounted for rotation with respect to mounting plate 122. Occlusion bed 130 is slidably mounted for movement toward and away from rotor assembly 120, e.g., by sliding on mounting plate 122, or another base structure, between rails 133, 134. Occlusion bed 130 has curved tubing interface surface 136 that, during peristaltic pump operation and rotation of rotor assembly 120, serves as a stationary curved surface against which the rollers press tubing 155 loaded in the occlusion pathway to advance and pump fluids in the tubing. The occlusion bed geometry and properties are as described previously in this application. Door 140 is mounted to hinge brackets 144 for pivoting the door toward and away from rotor assembly 120. Hinge bracket(s) 144 are generally mounted to mounting plate 122 or another structure that remains stationary during operation of the motor. In the embodiments illustrated in FIGS. 6 and 7, opposing hinge brackets 144 are provided and mount directly to door 140 or indirectly to a door frame 142 for rotation of the door around pivot axis 146.

A linkage assembly provides the connection between the pivoting door and sliding occlusion bed in the embodiments shown in FIGS. 6-9B. In the embodiment illustrated in FIG. 6, two occlusion bed frame members 172, 174 incorporating mounting brackets 173, 175 that contact (directly or indirectly) and mount to surfaces of sliding occlusion bed 130 on opposite sides of a centerline of the occlusion bed. In an alternative embodiment, a unitary occlusion bed frame member may contact a surface of sliding occlusion bed 130 opposite the occlusion surface substantially along its length and incorporate mounting brackets similar to those shown in FIG. 6. The mounting brackets or occlusion bed frame member may provide a highly rigid support structure having greater stiffness properties than those of the tubing interface surface of occlusion bed 130, as described previously, and may form part of an integral occlusion bed assembly.

Mounting brackets 173, 175 provide pivotable mounting of one end of linkage bars 176, 178 for pivoting around a common pivot axis 180. The opposite ends of linkage bars 176, 178 are pivotably mounted in brackets 177, 179 associated with the door and/or door frame around a common pivot axis 185. Shoulder screws mounting each end of each of the linkage bars to the appropriate bracket may act as both hinges and bearings. As the door is pivoted toward the rotor assembly and toward a closed position (e.g., following placement of tubing in the occlusion pathway), the door brackets, linkage bars, occlusion bed frame and occlusion bed move toward the rotor assembly to position the occlusion bed against the tubing for operation of the pump. As the door is pivoted away from the rotor assembly toward an open position (e.g., following a pumping operation), the door brackets, linkage bars, occlusion bed frame and occlusion bed move away from the rotor assembly to draw the occlusion bed away from the tubing, allowing removal of the tubing from the occlusion pathway.

Figure 9A:
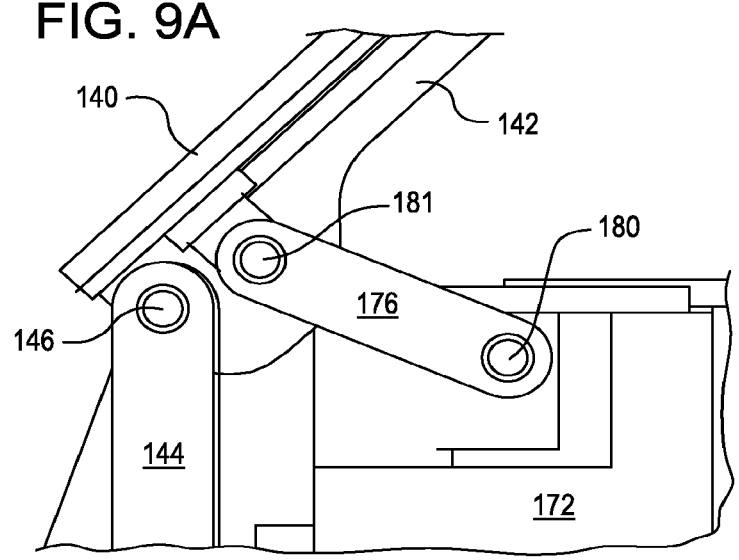
FIGS. 9A and 9B show enlarged side perspective views of the linkage mechanism and the arrangement of the linkage mechanism with respect to the pivoting door and occlusion bed when the pivoting door is in the open and closed condition.
Figure 9B:
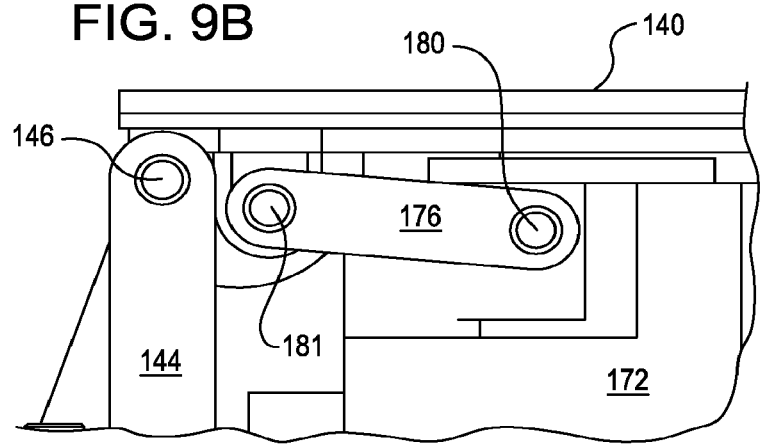
Figure 10A:
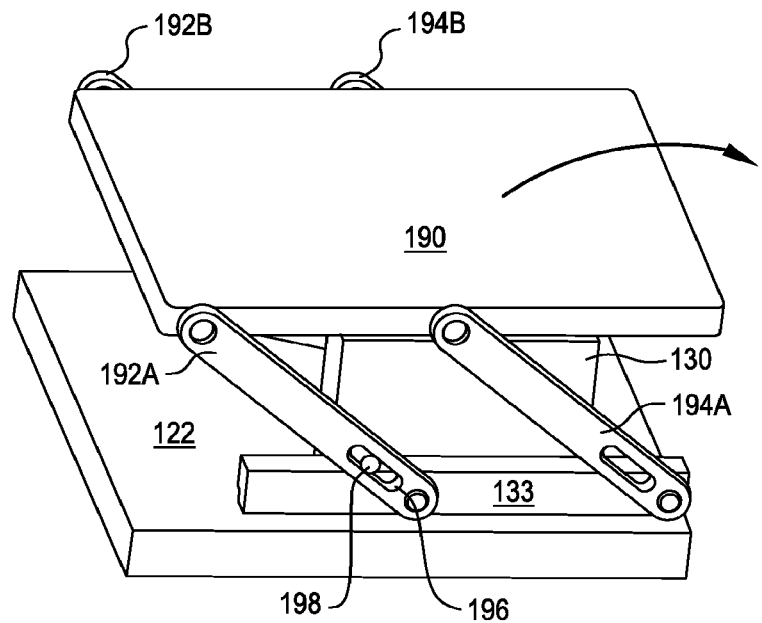
FIGS. 10A and 10B show side perspective views of another embodiment of a pump assembly of the present invention having a slidable door linked to a sliding occlusion bed.
Figure 10B:
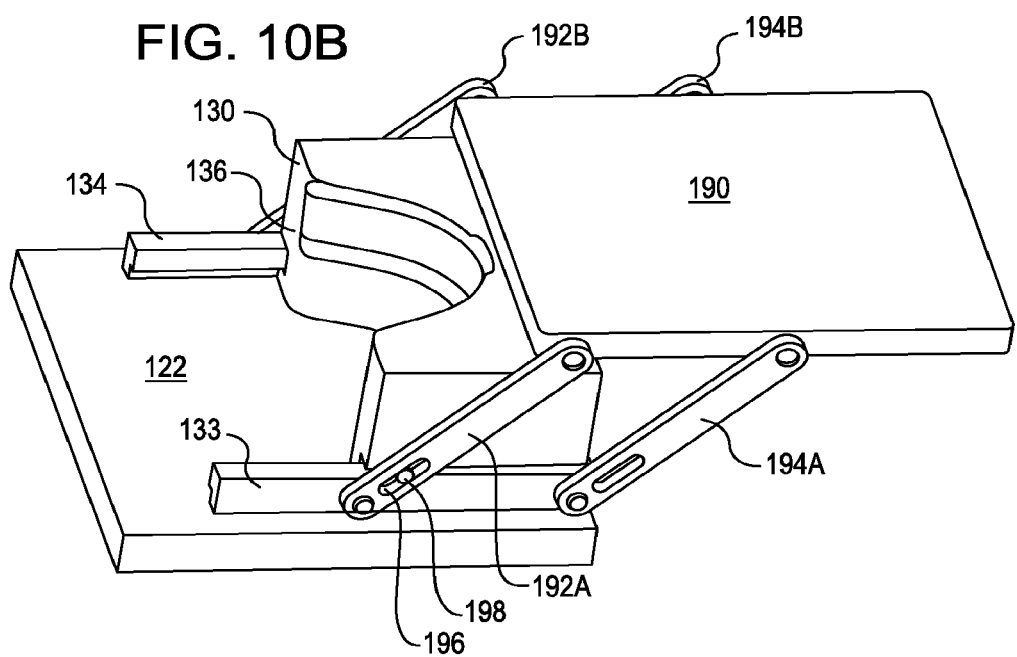

The hinge point positions of the linkage bars and the door bracket may be adjusted, as desired, to change the force curve and to provide a linear or a non-linear actuation relationship between the angle of the pivoting door and the position of the occlusion bed. FIGS. 9A and 9B show one embodiment of a preferred arrangement of rotational axes of the bar linkage and pivoting door that provides an over-center feature and non-linear actuation relationship between the angle of the pivoting door and the position of the occlusion bed. In the door open condition, when the door is rotated away from the rotor assembly, as shown in FIG. 9A, the occlusion bed pathway is open and the occlusion bed is positioned generally away from the rotor assembly. In this door open condition, the pivot axis 181 of the bar linkage at the door bracket is on one side of, seen as above in FIG. 9A, the pivot axis 146 of the door in bracket 144, while the pivot axis 180 of the bar linkage at the occlusion bed frame bracket 172 is on the other side of the pivot axis 146 of, shown as below in FIG. 9A. In the door closed condition, as shown in FIG. 9B, when the door is rotated toward the rotor assembly and the occlusion bed passage is closed against tubing, both of bar linkage pivot axes 180, 185 are located on the same side of, shown as below, the door pivot axis 146. In another embodiment, the pivot axis 181 of the bar linkage 176 at the door bracket is positioned below a line joining the pivot axis 146 of the door 144 and the pivot axis 180 of the bar linkage at the occlusion bed frame bracket when the door is in a closed position. This provides an "over-center" feature that results in progressively greater mechanical advantage (i.e. progressively less force required for door pivoting and occlusion bed movement) as the door approaches the close position and the occlusion bed approaches, and contacts, tubing in the occlusion pathway, and facilitates positive and secure positioning of the door in the closed condition, reducing the chance of the door opening during operation of the pump.

Pump assemblies incorporating the linkage mechanism described with reference to FIGS. 6-9B may additionally incorporate an adjustment mechanism for changing the occlusion bed dimensions or gap, a latching mechanism, one or more sensor(s), and the like, all as described in connection with the pump assemblies previously described herein.

FIGS. 10A-B and 11A-B schematically illustrate alternative embodiments of linkage mechanisms for moving an occlusion bed toward and away from the rotor assembly as a door slides between open and closed positions, exposing and covering the occlusion pathway, respectively. In the embodiments shown in FIGS. 10A-B and 11A-B, occlusion bed 130 having curved tubing interface surface 136 is slidably mounted for movement toward and away from a rotor assembly (not shown) by sliding with respect to mounting plate 122 between rails 133, 134, as described previously. One or more pairs of linkage beams 192A, 192B, 194A, 194B are pivotably mounted, directly or indirectly, at one end to sliding door 190 and at the other end to rails 133, 134 or another structure that remains stationary as the occlusion bed and sliding door travel.

One or more of the linkage beams, and preferably at least one pair of linkage beams, is also linked to sliding occlusion bed 130. In the embodiment illustrated in FIGS. 10A and 10B, at least one pair of linkage beams, e.g., 192A, 192B, incorporates a slot 196 in which a pin 198 or another structure mounted to or forming part of occlusion bed 130 travels. Thus, in this embodiment, door 190 may be positioned to close or prohibit access to the occlusion pathway in a closed position, shown in FIG. 10A, when the linkage beams are angled in one direction. Door 190 slides, to the right in the embodiments shown in FIGS. 10A and 10B, to provide access to the occlusion bed and expose the occlusion pathway. As the door slides to the open position, the linkage beams pivot through an angular path and pin 198 slides in slot 196 to translate occlusion bed 130 (e.g., away from the rotor), providing access to the occlusion pathway. Sliding of door 190 in the opposite direction reverses the motions, translates occlusion bed 130 in the opposite direction (e.g., toward the rotor), and covers the occlusion pathway.

Figure 11A:
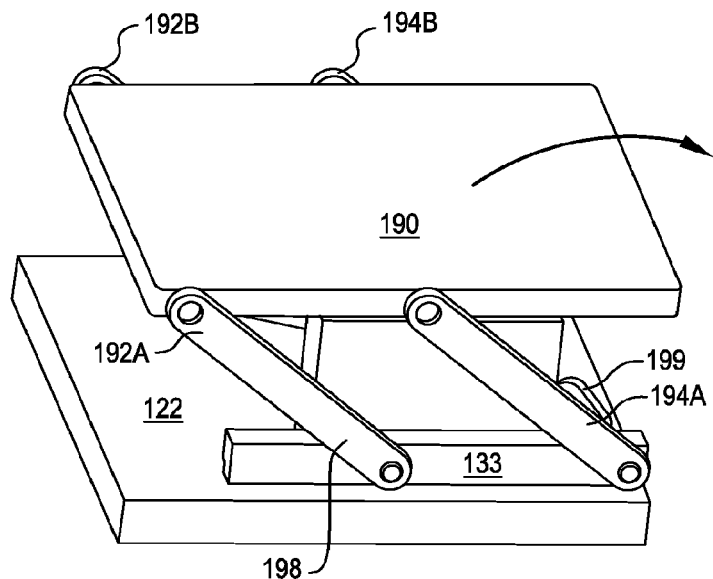
FIGS. 11A and 11B show side perspective views of yet another embodiment of a pump assembly of the present invention having a slidable door linked to a sliding occlusion bed.
Figure 11B:
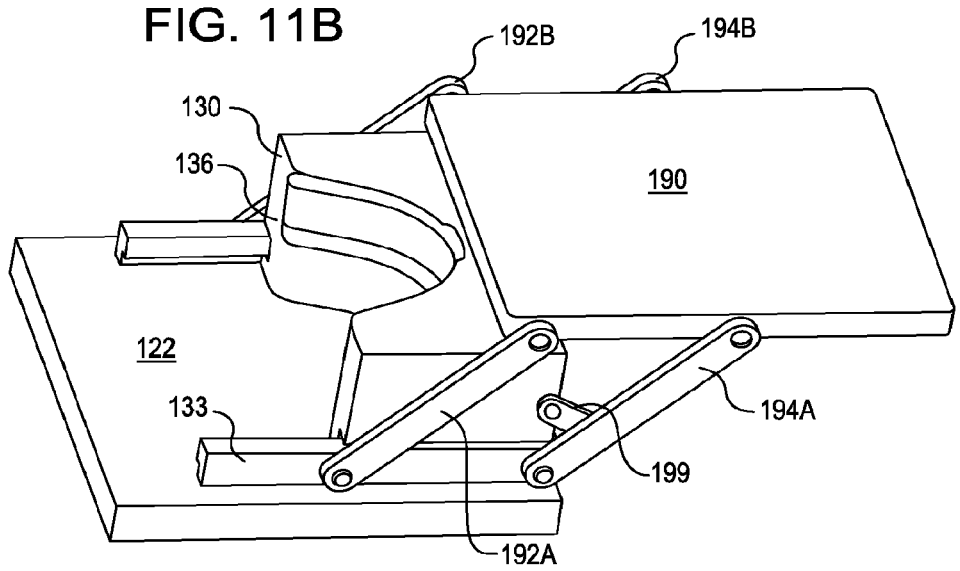

In the embodiment illustrated in FIGS. 11A and 11B, at least one of the linkage beams, and preferably at least one pair of linkage beams, e.g. 194A, 194B, is mounted to another pivoting linkage 199 that is also pivotably mounted, directly or indirectly, to occlusion bed 130. Thus, in this embodiment, door 190 may be positioned to close or prohibit access to the occlusion pathway in a closed position, shown in FIG. 11A, when the linkage beams are angled in one direction. Door 190 slides, to the right in the embodiments shown in FIGS. 11A and 11B, to provide access to the occlusion bed and expose the occlusion pathway. As the door slides to the open position, the associated linkage beam pivots with respect to pivoting linkage 199, and then slides the pivoting linkage 199 and occlusion bed 130 in the direction of motion of door 190. By this combination of pivoting and translation of pivoting linkage 199 with sliding of door 190 toward an open position and then opposite direction, the occlusion bed is translated with respect to support plate 122 (and the rotor) to open and close the occlusion pathway. Sliding of door 190 in the opposite direction reverses the motions, translates occlusion bed 130 in the opposite direction (e.g., toward the rotor), to close and cover the occlusion pathway.

Figure 12A:
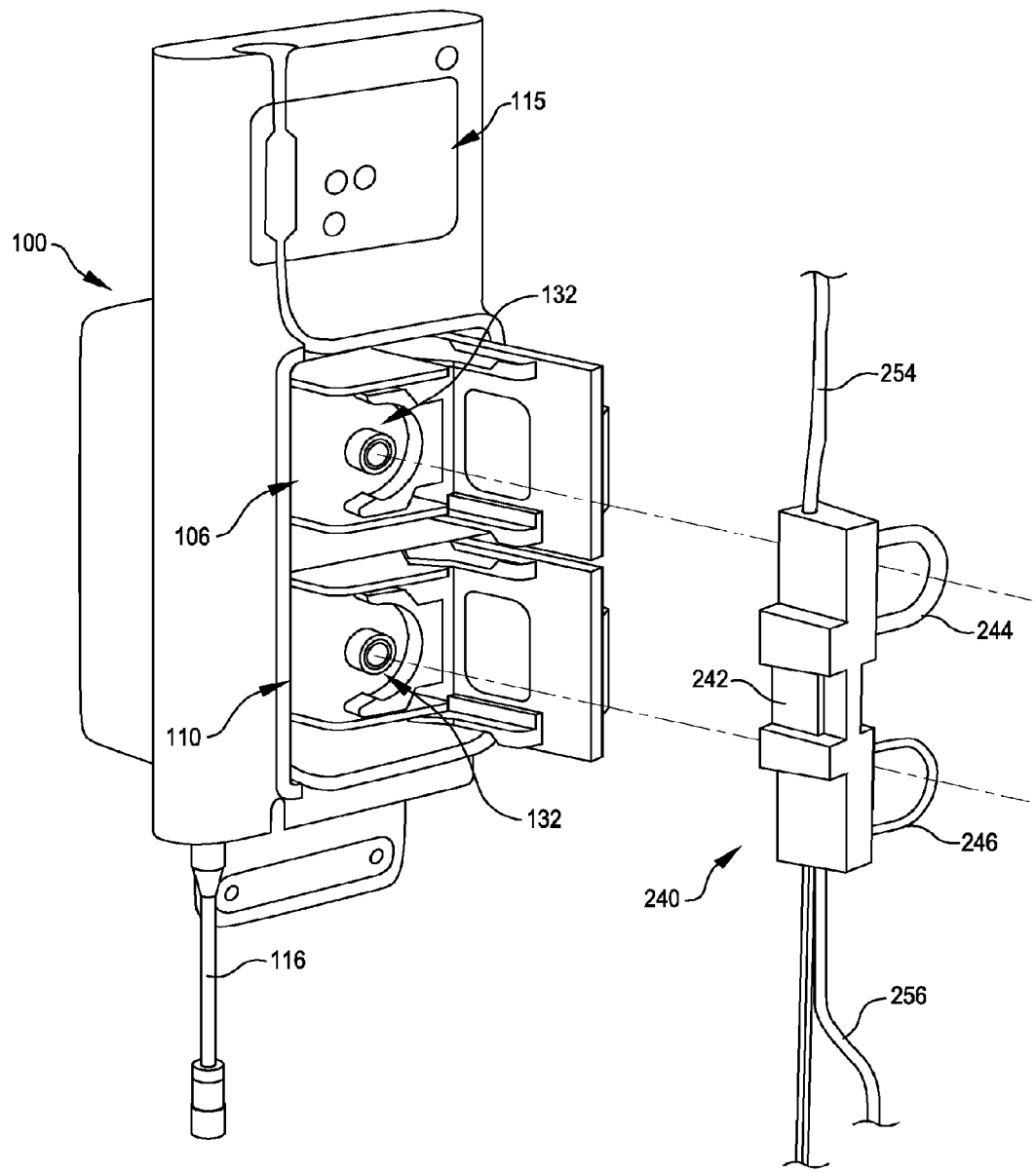
FIG. 12A shows a schematic view illustrating the interface of an adaptive tubing cassette with aspiration and infusion systems incorporated in a control console as illustrated in FIG. 1.
Figure 12B:
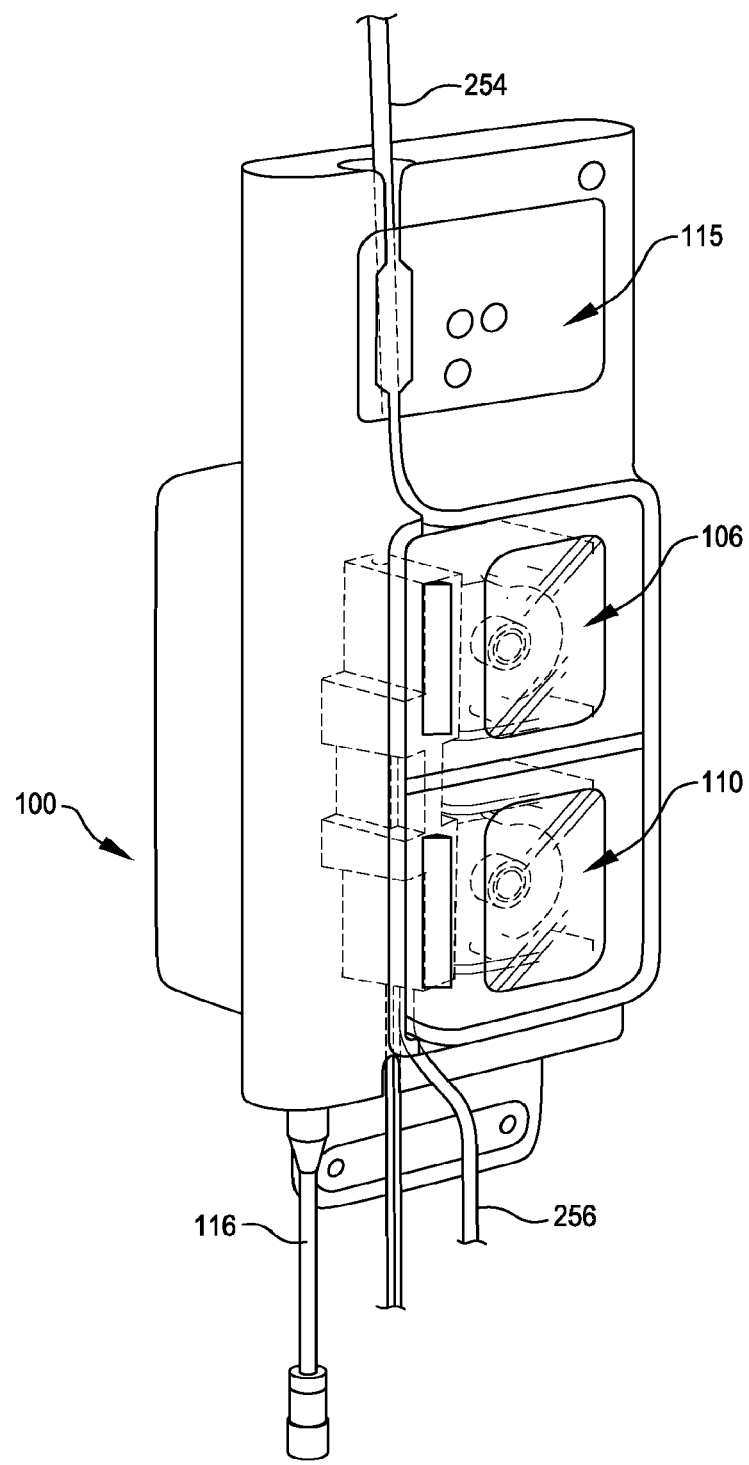
FIG. 12B shows another schematic view illustrating the adaptive tubing cassette shown in FIG. 12A stably mounted in aspiration and infusion systems incorporated in the control console, with exterior doors closed.

Pump assemblies of the present invention may be incorporated in medical devices, control consoles, and the like, as illustrated in FIG. 1 herein. Adaptive tubing components and tubing cassettes may be provided in connection with such devices and the pumps described herein to facilitate positioning of appropriate tubing within the pump assembly occlusion pathways. Exemplary adaptive tubing components and their installation in pump assemblies, control consoles and medical devices of the present invention are illustrated in FIGS. 12A and 12B. Adaptive tubing cassette 240 interfaces with the aspiration and/or infusion systems provided in control module 100 and comprises a housing component 242 and two preformed tubing loops 244, 246 sized and configured to insert into and mate with infusion and aspiration systems housed in control console 100. Tubing loops 244, 246, in the embodiment shown, are sized and configured to insert into and mate with a tubing pathway, or occlusion bed pathway 132, provided in peristaltic pump assemblies housed in the control console. Infusion tubing loop 244 is in fluid communication with infusion tubing and infusate source tubing 254, which is connected or connectable to an infusate source or reservoir. Aspiration tubing loop 246 is in fluid communication with aspiration tubing 256 connected or connectable to aspirate collection receptacle. Adaptive tubing cassette housing component 242 provides a structure for grasping and manipulation by an operator and also incorporates an interface structure sized and configured to mate, such as mechanically and/or electronically, with a receiving structure provided on control console 100 in proximity to the aspiration and/or infusion systems.

Figure 13A:
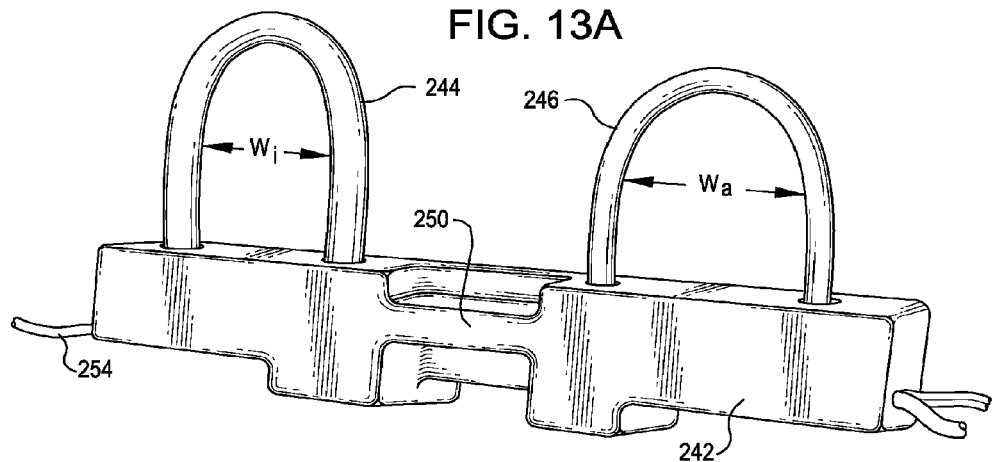
FIG. 13A shows a side perspective view of an exemplary interventional catheter tubing cassette adapted for mating with and stably mounting to aspiration and infusion systems incorporated in a control console.
Figure 13B:
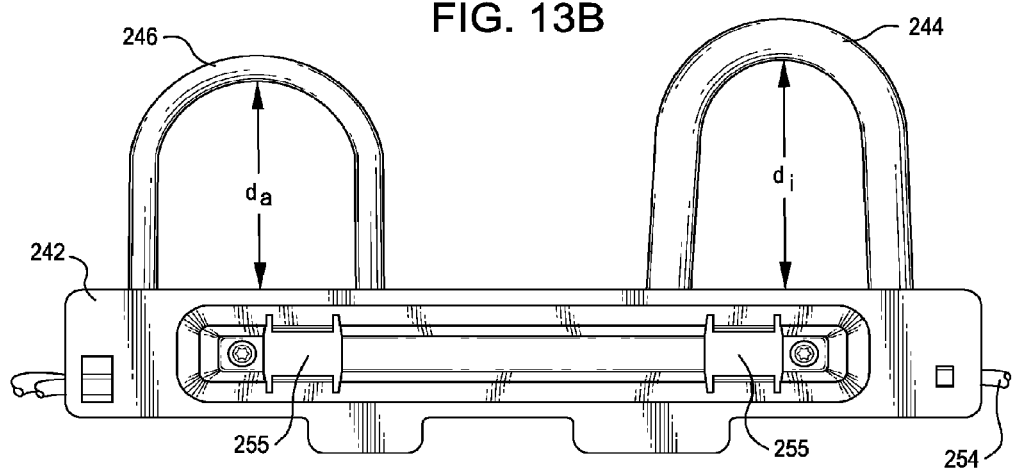
FIG. 13B shows another side view of the exemplary interventional catheter tubing cassette of FIG. 13A illustrating a mechanical mating system for mounting the tubing cassette in a mating receiving structure provided in the console in connection with the aspiration and infusion systems.

FIGS. 12A and 12B show enlarged schematic diagrams illustrating an adaptive tubing cassette 240 in position for mounting (FIG. 12A) and mounted (FIG. 12B) in infusion and aspiration systems on control console 100, and FIGS. 13A-13C show various views of adaptive tubing cassette 240. During operation of an associated medical device, such as an interventional catheter assembly, infusion tubing 254 accesses the infusate source(s) and, prior to entry into tubing cassette housing 242, may incorporate an optional valve 255 (See, e.g., FIG. 13C) comprising a self sealing membrane for withdrawing fluids (or gas) from the infusion tubing line 254, or for introducing fluids to the infusion tubing line 254. Suitable bubble detector(s) may also be provided in conjunction with infusion tubing to detect and/or prevent entrainment of bubbles that would be harmful to patients. Infusion tubing 254 is in sealed fluidic communication with preformed infusion tubing loop 244 at an infusate entry portion 243 of preformed infusion tubing loop 244, and infusion tubing loop 244 is in sealed fluidic communication with interventional catheter infusion tubing 234 at an infusate exit portion 245 of preformed infusion tubing loop 244.

In some embodiments, infusion tubing 254, preformed infusion tubing loop 244 and interventional catheter infusion tubing 234 may comprise tubing having the same or similar properties and dimensions. In other embodiments, such as when infusion system 106 comprises a high pressure infusion pump, preformed infusion tubing loop 244 comprises a thicker walled, generally stiffer tubing material than the tubing of infusion tubing 254 or 234. Preformed infusion tubing loop 244 is configured to mate with a pump assembly occlusion pathway 132 in infusion system 106 that, when the pump is operating, retains the tubing as pump rollers operate to advance infusate through the tubing at a generally high pressure and volume. In one embodiment, desired infusate rates of up to about 150 ml/min at infusate pressures of up to 160 psi are provided by infusion pump system 106. Preformed infusion tubing loop 244 is designed to withstand the generally high infusate pressures generated at infusion pump system 106.

Aspiration tubing loop 246 is configured to mate with a pump assembly occlusion pathway 132 in aspiration system 110 that, when the pump is operating, retains the tubing as pump rollers operate to advance aspirate through the tubing at generally moderate pressures and volumes. In one embodiment, desired aspiration rates of up to about 90 ml/min at aspiration pressures of up to 25 psi are provided by infusion pump system 106. In some embodiments, aspiration tubing 256 and preformed aspiration tubing loop 246 may comprise tubing having the same or similar properties and dimensions. Preformed aspiration tubing loop 246 generally comprises a thinner walled, generally more flexible tubing than preformed infusion tubing loop 244.

In some embodiments, preformed tubing loops 244 and 246 comprise different tubing materials and have a different configuration, as shown. As can be seen in FIGS. 13A and 13B, for example, the outer diameter of preformed infusion tubing loop 244 is larger than the outer diameter of preformed aspiration tubing loop 246. In addition, preformed infusion tubing loop 244 extends a greater distance $d_i$ from an edge of housing 242 than the distance $d_a$ of preformed aspiration tubing loop 246 from an edge of housing 242. The width of preformed infusion tubing loop 244 W; may also be less than the width $W_a$ of preformed aspiration tubing loop 246.

Tubing cassette housing 242 has a size and configuration suitable for housing the various infusate and aspirate tubing components in a convenient and kink-free manner and provides a convenient, exposed user grasping surface. The user grasping surface may incorporate a handle 250 in a central portion of the housing, between preformed tubing loops 244 and 246 and oriented for grasping on a surface substantially orthogonal to the plane of the preformed tubing loops. Handle 250 may be formed by adjacent recesses, or indentations, providing convenient access and grasping.

The face of tubing cassette housing 242 generally opposite handle 250, which is substantially orthogonal to the plane of preformed tubing loops on the opposite side, preferably incorporates at least one mechanism for detachably mating with the control console in the area of the infusion and/or aspiration systems. This mating system may comprise a mechanical mating structure(s) provided on tubing cassette housing 242 such as keyed recesses 255, sized and configured to interlock with mating structures provided on the control console in proximity to infusion and aspiration systems 106, 110, respectively. Keyed recesses 255 and the mating structures provided on the control console provide a stable, and preferably detachable mounting of tubing cassette housing 242 on the control console. While mechanically interlocking structures are illustrated and described, it will be appreciated that other types of mechanical and/or electronic structures may provide the desired detachable interlocking features.

FIG. 13C illustrates, in addition to the various fluid tubing components residing in adaptive tubing cassette 240, an electrical or electronic interface component 260. Electronic interface component 260 may comprise a data storage device 261 providing authentication and/or operating instruction protocols and cable 262 terminating in an interface 263. Interface 263 may communicate following connection to a mating interface provided on control console 100 or an intermediate interface component.

Figure 14:
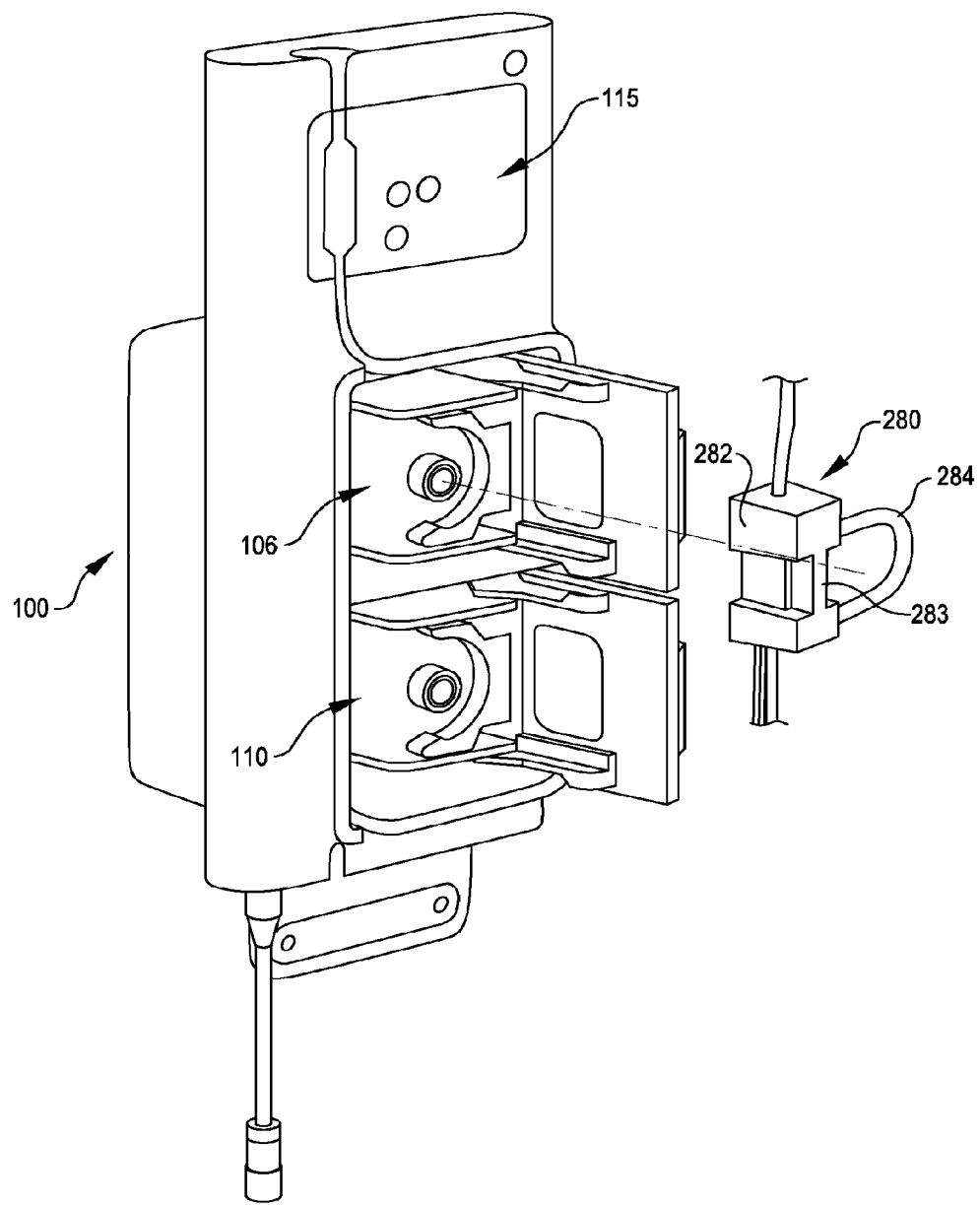
FIG. 14 shows a schematic view illustrating the interface of another adaptive tubing cassette with an aspiration or infusion system incorporated in a control console as illustrated in FIG. 1.
Figure 15A:
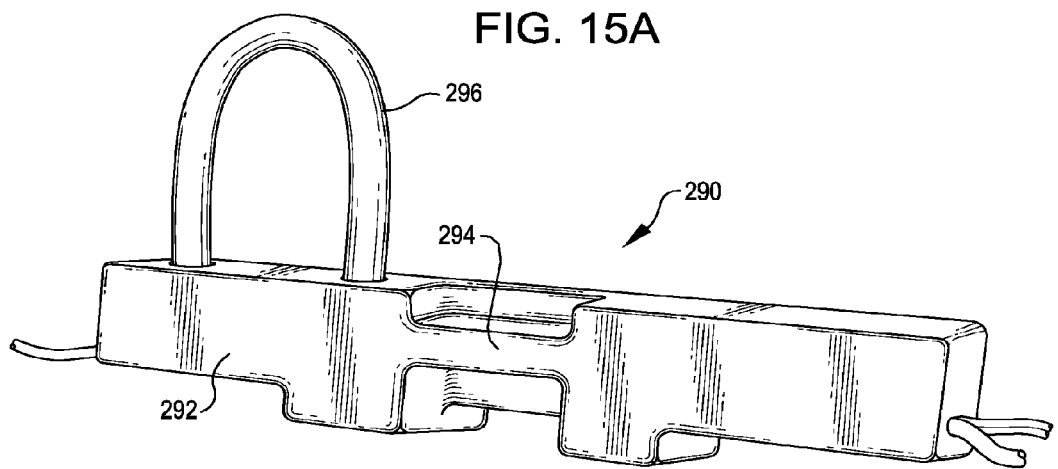
FIG. 15A shows a schematic view illustrating another embodiment of an adaptive tubing cassette suitable for use with an interventional catheter assembly having infusion capability.
Figure 15B:
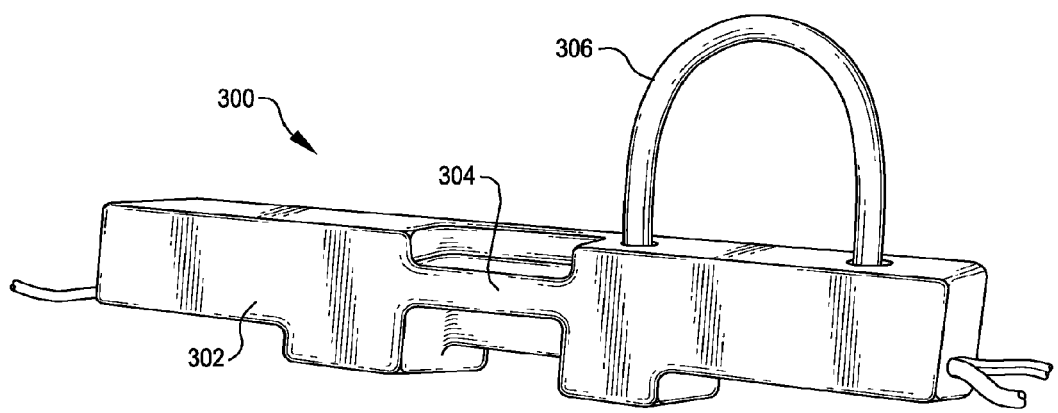
FIG. 15B shows a schematic view illustrating another embodiment of an adaptive tubing cassette suitable for use with an interventional catheter assembly having aspiration capability.

FIG. 14 illustrates an alternative embodiment of a preformed tubing cassette 280 according to the present invention comprising housing 282 having a centrally positioned handle 283 and a single preformed tubing loop 284. In alternative embodiments, tubing loop 284 may be sized and configured for mating with a tubing pathway formed as part of an infusion or aspiration system. This type of preformed tubing cassette having a single preformed tubing loop may be used, for example, with interventional catheter assemblies having either infusion or aspiration capabilities, but not both, and may otherwise interface with control console 100 similarly to the interface of adaptive tubing cassette 240, described above.

FIGS. 13A and 13B illustrate alternative embodiments of adaptive tubing cassettes 290 and 300, respectively, having housings 292 and 302, respectively, sized and configured for detachably mating with the control console in the area of the infusion and/or aspiration system(s). Adaptive tubing cassettes 290 and 300 have a central handle 294, 304 for grasping and incorporate preformed tubing loops 296, 306, respectively. Adaptive tubing cassette 290 is designed for use with an infusion (only) interventional catheter assembly; adaptive tubing cassette 300 is designed for use with an aspiration (only) interventional catheter assembly.

While the present invention has been described above with reference to the accompanying drawings in which particular embodiments are shown and explained, it is to be understood that persons skilled in the art may modify the embodiments described herein without departing from the spirit and broad scope of the invention. Accordingly, the descriptions provided above are considered as being illustrative and exemplary of specific structures, aspects and features within the broad scope of the present invention and not as limiting the scope of the invention.

What is claimed is:

1. An adaptive tubing cassette for use in connection with an interventional catheter assembly, comprising:
 a handle component having an interface region adapted to mount stably in a mating interface region of a control console;
 a first preformed tubing section and a second preformed tubing section, each of the preformed tubing sections being in the form of a loop, mounted to and extending from a common side of the handle component, the first and second preformed tubing sections being adapted to mount stably in tubing receiving pathways provided in connection with the control console; wherein the first preformed tubing section is configured to withstand a higher burst pressure than the second preformed tubing section.

2. The adaptive tubing cassette of claim 1, wherein at least one of the first or the second preformed tubing sections includes an infusion tubing section and is designed to withstand infusate rates of up to 150 ml/min.

3. The adaptive tubing cassette of claim 1, wherein at least one of the first or the second preformed tubing sections includes an infusion tubing section and is designed to withstand infusate pressures of up to 160 psi.

4. The adaptive tubing cassette of claim 1, wherein at least one of the first or the second preformed tubing section includes an aspiration tubing section and is designed to withstand aspiration rates of up to 90 ml/min.

5. The adaptive tubing cassette of claim 1, wherein at least one of the first or the second preformed tubing section includes an aspiration tubing section and is designed to withstand aspiration pressures of up to 25 psi.

6. The adaptive tubing cassette of claim 1, wherein the first preformed tubing section includes a first flexibility and wherein the second preformed tubing section includes a second flexibility, and wherein the first flexibility is different than the second flexibility.

7. The adaptive tubing cassette of claim 1, wherein a width of the first preformed tubing loop is less than a width of the second preformed tubing loop.

8. The adaptive tubing cassette of claim 1, wherein the first preformed tubing loop has a larger outer diameter than the second preformed tubing loop.

9. The adaptive tubing cassette of claim 1, wherein the first preformed tubing loop extends a greater distance from an edge of the handle component than the second preformed tubing loop.

10. The adaptive tubing cassette of claim 1, wherein at least one of the preformed tubing sections is capable of withstanding infusate rates of up to 150 ml/min at infusate pressures of up to 160 psi.

11. The adaptive tubing cassette of claim 1, wherein the first preformed tubing loop includes a first material and wherein the second preformed tubing loop includes a second material, and wherein the first material is different than the second material.

12. The adaptive tubing cassette of claim 1, wherein the first preformed tubing loop includes a first tubing wall thickness, and wherein the second preformed tubing loop includes a second tubing wall thickness, and wherein the first tubing wall thickness is different from the second tubing wall thickness.

13. The adaptive tubing cassette of claim 12, wherein the first tubing wall thickness is greater than the second tubing wall thickness.

14. An adaptive tubing cassette for use in connection with an interventional catheter assembly, comprising:
 a handle component having an interface region;
 a first preformed tubing section and a second preformed tubing section, each of the first and second preformed tubing sections extending from the handle component, the first and second preformed tubing sections being configured to be disposed within a control console;
 wherein the first preformed tubing section has a first burst pressure, and wherein the second preformed tubing section has a second burst pressure different from the first burst pressure.

15. The adaptive tubing cassette of claim 14, wherein the first preformed tubing section includes a first flexibility and wherein the second preformed tubing section includes a second flexibility, and wherein the first flexibility is different than the second flexibility.

16. The adaptive tubing cassette of claim 14, wherein the first preformed tubing section includes a first material and wherein the second preformed tubing section includes a second material, and wherein the first material is different than the second material.

17. The adaptive tubing cassette of claim 14, wherein the first preformed tubing section includes a first tubing wall thickness, and wherein the second preformed tubing section includes a second tubing wall thickness, and wherein the first tubing wall thickness is different from the second tubing wall thickness.

18. The adaptive tubing cassette of claim 14, wherein a width of the first preformed tubing section is less than a width of the second preformed tubing section.

19. The adaptive tubing cassette of claim 14, wherein the first preformed tubing section has a larger outer diameter than the second preformed tubing section.

20. A peristaltic pump system, comprising:
- a control console having an infusion system and an aspiration system;
- an adaptive tubing cassette including a handle member, an infusion tube, and an aspiration tube, wherein the infusion tube and the aspiration tube extend from the handle member;
- wherein the adaptive tubing cassette is designed to engage a receiving region of the infusion system and a receiving region of the aspiration system;
- wherein the receiving region of the infusion system is designed to accept the infusion tube, and wherein the infusion tube has a first burst strength; and
- wherein the receiving region of the aspiration system is designed to accept the aspiration tube, and wherein the aspiration tube has a second burst strength different from the first burst strength.

\* \* \* \* \*